(12) United States Patent
Dye et al.

(10) Patent No.: US 6,875,218 B2
(45) Date of Patent: *Apr. 5, 2005

(54) ELONGATED DRIVING BIT ATTACHABLE TO A DRIVING INSTRUMENT AND METHOD OF USE FOR MINIMALLY INVASIVE HIP SURGERY

(75) Inventors: Donald Dye, Pflugerville, TX (US); Eric J. Schantz, Austin, TX (US)

(73) Assignee: Zimmer Austin, Inc., Austin, TX (US)

(*) Notice: Subject to any disclaimer, the term of this patent is extended or adjusted under 35 U.S.C. 154(b) by 136 days.

This patent is subject to a terminal disclaimer.

(21) Appl. No.: 10/375,453
(22) Filed: Feb. 27, 2003
(65) Prior Publication Data
US 2004/0030344 A1 Feb. 12, 2004

Related U.S. Application Data

(60) Provisional application No. 60/387,492, filed on Jun. 10, 2002.

(51) Int. Cl.[7] ............................................... A61B 17/58
(52) U.S. Cl. ............................................................ 606/91
(58) Field of Search .............................. 606/91, 99, 81, 606/86, 80, 180; 623/22.21, 22.12, 22.24, 22.25, 22.28; 128/898

(56) References Cited

U.S. PATENT DOCUMENTS

| 4,305,394 A | * | 12/1981 | Bertuch, Jr. | 606/91 |
| 5,037,424 A | * | 8/1991 | Aboczsky | 606/91 |
| 5,584,837 A | * | 12/1996 | Petersen | 606/91 |
| 5,683,399 A | * | 11/1997 | Jones | 606/91 |
| 5,904,689 A | * | 5/1999 | Jonjic | 606/99 |
| 6,695,850 B2 | * | 2/2004 | Diaz | 606/91 |

* cited by examiner

Primary Examiner—Pedro Philogene
(74) Attorney, Agent, or Firm—Jonathan D. Feuchtwang

(57) ABSTRACT

A method and apparatus for performing minimally invasive hip surgery for implanting a prosthetic acetabular component into a natural acetabulum. The method and apparatus include a driving bit having one end connectable to an angled driving instrument and another end connectable to a screw-hole plug, dome plug, or bone screw. The driving bit has an elongated body with a length adapted for use in minimally invasive acetabular surgery.

20 Claims, 2 Drawing Sheets

ELONGATED DRIVING BIT ATTACHABLE TO A DRIVING INSTRUMENT AND METHOD OF USE FOR MINIMALLY INVASIVE HIP SURGERY

CROSS-REFERENCE TO RELATED APPLICATIONS

This application claims benefit of priority of U.S. Provisional Application Ser. No. 60/387,492 filed Jun. 10, 2002.

FIELD OF THE INVENTION

The disclosure herein generally relates to a method and apparatus performing minimally invasive hip replacement surgery for the acetabulum using an elongated driving bit that is attachable to a driving instrument.

BACKGROUND OF THE INVENTION

Traditional hip replacement surgery has been used in the United States since as early as the 1960's. The surgical technique to implant a hip has not drastically changed over the years, and today, this technique is quite successful. In fact, the surgical technique is prolifically used throughout the world and has a known success rate of over 90%. Certainly, the traditional surgical technique is fundamentally sound and predictable.

Unfortunately, traditional techniques to implant a hip have well recognized shortcomings. Most importantly, a rather large incision is made on the side of the hip. The incision can extend from 6 to 12 inches; the actual length of the incision depends on the size of the patient and type of surgery (revision versus total hip arthroplasty, for example). A long, deep incision can divide a number of important stabilizing muscles and tendons and further damage the hip joint and surrounding soft tissue. Inevitably, long incisions lead to larger blood losses, longer rehabilitation times for patients, and unsightly scar lines. A patient can easily spend four or five days in the hospital after a total hip arthroplasty, for example.

Recently, surgeons have been developing new, less invasive surgical techniques to perform total hip arthroplasty and revision hip surgery. Minimally invasive surgery, or MIS, is one such technique with great promise to become a popular and accepted technique for implanting a hip.

MIS has significant advantages over traditional hip replacement surgery. Most importantly, a rather small incision is made on the side on the hip. This incision is approximately 3 to 5 inches long, and the benefits of a shorter incision are enormous.

First and foremost, the patient can recover in a much shorter period of time after a MIS. The recuperation time in the hospital can be a few days and significantly reduce the cost to both the patient and hospital. In fact, some patients are leaving the hospital within 24 to 48 hours after the surgery. Obviously, this shortened time period is extremely important to the patient.

As another advantage, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Presently, instruments to perform MIS are being developed and refined. These instruments have a vital role in the ability to perform a successful minimally invasive surgery. These instruments, for example, must enable the surgeon to place the hip implant in a very precise location. If the implant is not accurately placed, then complications, such as dislocation or subluxation, can occur. Further and most importantly, the instruments must consistently and reliably perform through a small three inch opening in the patient.

A successful design of instruments for MIS has other challenges as well. Specifically, the instrument must be easy to use and facilitate the implantation procedure. If the MIS instrumentation is too cumbersome or not easy to manipulate, then the surgeon will be less likely to use minimally invasive surgery. The patient, then, will not reap the benefits MIS has to offer.

As yet another consideration, MIS instrumentation must appeal to a wide range of orthopedic surgeons with various skills and experience. If, for example, the instruments are too complex and complicated, then they will not be appealing and accepted in the orthopedic surgical community. Further yet, the training and skill level required to use the instruments and become proficient with them, cannot be overly taxing on the orthopedic surgeons.

While implanting or repairing a prosthetic acetabular shell in MIS for instance, screw-hole plugs and dome plugs must be screwed in the acetabular shell. Further, bone screws must be driven through screw-holes in the acetabular shell and into surrounding cortical bone to secure the shell to this bone. Traditional surgical driving instruments, though, are not shaped and sized to engage a screw-hole plug or bone screw and place it through the acetabular shell. For one reason, the screw-hole openings in the acetabular shell are at an angle with respect to the surgical site. Further, these screw-hole openings are deep in the surgical site and relatively far from the entrance of the incision. Thus, a straight driving instrument will not have the proper angulation to reach the screw-hole opening in the shell. Further, a short driving bit attached to the end of a driving instrument will not be able to reach the screw-hole openings.

Great care must be taken while placing a screw-hole plug or dome plug in the acetabular shell. If the threads on the plug do not properly align with the threads in the shell, then these threads can become stripped or cross-threaded. In such instances, the acetabular shell may have to be removed and replaced during the surgical procedure. Further yet, great care must be taken while placing a bone screw through the screw-hole opening in the acetabular shell. If the bone screw is not placed with the correct angle, then the bone screw may not seat well in the screw-hole opening. Additionally, the bone screw may not properly engage cortical bone to hold the shell in place in the acetabulum. Further yet, if the driving bit is not long enough, then the bone screw may not be placed deeply enough into the acetabulum.

In short, instruments, and in particular driving instruments and driving bits attachable to screw-hole plugs and bone screws, play a vital role in MIS surgery for hip implantation. It therefore would be advantageous to provide a new method and accompanying instruments for driving and aligning screw-hole plugs and bone screws in minimally invasive surgery to implant a prosthetic hip.

SUMMARY OF THE INVENTION

The present invention is directed to a method and apparatus for performing minimally invasive hip replacement surgery for the acetabulum using an elongated driving bit. A proximal end of the driving bit is attachable to a driving instrument, such as a fixed angle driver. A distal end of the driving bit is attachable to a screw-hole plug, dome plug, bone screw, or the like.

The method of the present invention generally comprises the steps of templating the acetabulum to estimate the size of reamer and acetabular components; incising the surgical site with a single incision approximately three to five inches in length; retracting soft tissue at the surgical site; dislocating the hip from the acetabulum; reaming the acetabulum with a reamer; inserting and aligning a trial shell into the reamed acetabulum; inserting and aligning a trial insert to the trial shell; removing the trial insert and shell; inserting and aligning an implant shell into the reamed acetabulum; impacting the implant shell with a acetabular shell impaction instrument; providing a driving instrument; providing an elongated driving bit; connecting one end of the driving bit to the driving instrument; connecting another end of the driving bit to an acetabular plug or bone screw; aligning and inserting the plug or screw into the implant shell; inserting and impacting an implant insert into the implant shell; removing all instruments from the surgical site; and closing the surgical site.

One important advantage of the present invention is that the method and driving instrument are used in a minimally invasive orthopedic hip surgery. A single, small three to five inch incision is made at the surgical site on the side on the hip. The method of the present invention, thus, enjoys the benefits of a shorter incision compared to traditional hip surgery that uses a much longer incision. As one benefit, the patient can recover in a much shorter period of time after a MIS. The recuperation time in the hospital can be a few days and significantly reduce the cost to both the patient and hospital. This shortened time period is extremely important to the patient. Further, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Another important advantage of the present invention is that the driving bit is elongated. The extended length of the driving bit enables it to reach deep into the surgical site and engage a screw-hole opening in the acetabular shell. A traditional, short driving bit could not reach the shell in this manner through the small MIS incision.

Another advantage of the present invention is that the elongated driving bit is utilized with an angled driving instrument. The angle of the driving instrument enables the driving tip to reach the embedded shell even if the shell is disposed at an angle with respect to the surgical incision. The angulation of the driving instrument coupled with the elongated driving bit enable acetabular plugs and bone screws to be positioned into the acetabular shell and driven into place.

As a further advantage, the driving bit has a twisted hexagonal tip at the distal end. This tip is adapted to engage and hold an acetabular plug, bone screw, or the like. The twisted configuration frictionally locks with the plug or screw so it will not readily fall from the end of the driving bit. The plug or screw can, thus, be positioned into the small MIS incision and maneuvered through various angles around the surgical site without falling off or disengaging from the end of the driving bit.

The driving bit generally comprises an elongated cylindrical body that extends from a proximal end to a distal end. The proximal end has an interface or connection that is adapted to connect to a driving instrument, such as a fixed angle driver or a flexible angle driver. The distal end has a driving tip shaped as an interface or connection that is adapted to connect to an acetabular screw-plug, seal, dome plug, bone screw, or the like. Preferably, the driving tip is shaped as a twisted hexagon.

One critical element of the present invention is the length of the driving bit. Preferably, this length is about 1.25 inches and may have a range from about 0.37 inches to about 2.0 inches.

As another advantage, the driving bit can consistently and reliably perform through a small three to five inch opening in the patient. Importantly, the length of the driving bit is specifically adapted to pass through a small incision and reach an embedded acetabular shell.

Further yet, the driving bit is easy to use and facilitates the implantation procedure. The driving bit has a proximal end with a standard AO interface that readily attaches to a driving instrument. As such, use of the driving bit can appeal to a wide range of orthopedic surgeons with various skills and experience. Further yet, the training and skill level required to use the driving bit and accompanying instrument and become proficient with them is not overly taxing on the orthopedic surgeon.

DETAILED DESCRIPTION

The instruments, method, and steps of the present invention are now described in more detail. The method describes the steps to perform a minimally invasive surgery to implant a prosthetic acetabular component into the natural acetabulum of a patient while using an elongated driving bit connected to an angled driving instrument. Some of these steps described in the method are known to those skilled in the art and will not be discussed in great detail. Further, one skilled in the art will appreciate that certain steps may be altered or omitted while other steps may be added without departing from the scope of the invention. The novel steps of the present invention, for example, can be applied to total hip arthroplasty, to revision surgeries for total and partial hip replacement, and to other orthopedic hip surgeries using minimally invasive surgical techniques.

To facilitate a discussion of the present invention, the method of implanting a prosthetic acetabular component is divided into a plurality of steps or sections. Each of these sections is discussed seriatim.

More specifically, the method of the present invention teaches how to implant a prosthetic acetabular shell and insert into the natural acetabulum using an elongated driving bit that is attachable at one end to an acetabular plug or bone screw and attachable at another end to an angled driving instrument. For illustrative purposes, the discussion focuses on implanting a Converge™ Acetabular System of Centerpulse Orthopedics Inc. of Austin, Tex. This system illustrates one possible acetabular system that can be used. One skilled in the art will appreciate that other, different acetabular systems can also be used with the method and apparatus of the present invention without departing from the scope of the invention.

Templating the Acetabulum

Typically, the side of the acetabulum to be reconstructed is templated. Use of a template enables the surgeon to make an estimation of the size of reamers to be used and the size of acetabular component to be inserted. The acetabulum is templated on the both the anterior-posterior (A/P) and lateral radiographs. The hemisphere of the acetabular component is aligned with the mouth of the bony, natural acetabulum while simultaneously avoiding any osteophytes. On the A/P radiograph, the acetabular component should rest on the floor of the cotyloid notch and may touch the illoischial line. Further, the component should have a maximum lateral opening of about 40°. On the groin lateral radiograph, the cup size selected should contact the anterior and posterior rim of the bony, natural acetabulum and the medial subchondral bone. A correct position of the acetabular component will anatomically reproduce the center of rotation of the femoral head. If a bony defect is identified, use the correctly placed template to measure for proper size of the acetabular component and determine any need for bone graft.

Figure 1:
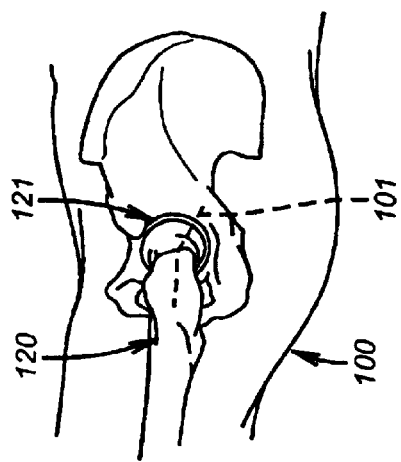
FIG. 1 is a view of a patient showing a femur and femoral head positioned in the acetabulum with an MIS incision marked along the hip.

Incising the Surgical Site (See FIG. 1)

A relatively small, single minimally invasive incision is made at the surgical site. A minimally invasive incision for this procedure has a length from about 2½ inches to about 4 or 5 inches. The incision is slightly curved or straight, commences near the vastus tubercle, and continues toward the greater trochanter and posterior inferior spine. The incision should be carried down through subcutaneous tissue and fascia lata. Any muscle tissue should be gently split in line with its fibers. At this time, a leg length measurement can be taken using techniques known in the art.

Providing Retractors

The retractors have an elongated, flat, thin body with two primary sections, a handle section and a retracting section. The handle section is elongated and adapted to be gripped with a hand. A smooth curved section transitions the handle section to the retracting section. The retracting section has a paddle with a prong that curves outwardly and away from the paddle and handle section.

Exposing the Acetabular Joint and Dislocating the Hip From the Acetabulum

Next, the knee is flexed, and the leg is internally rotated. Using a hot knife, the piriformis, short external rotators, quadratus femoris, and some posterior capsule are incised off the posterior trochanter to expose the lesser trochanter. Dislocation of the hip can now occur. A bone hook or skid may be used to avoid excess torsion on the femoral shaft.

At this time, retractors may be placed, for example under the femoral head or lesser trochanter, in order to achieve visualization for proper transection of the femoral neck if this procedure is desired at this time. If such transection occurs, the femoral neck should be transected at the templated level. Then retract the femur in an anterior direction to expose the acetabulum. Care should be taken to protect the sciatic nerve.

The retractor can be placed on the pelvis to hold the femur in an anterior position to the acetabulum. The capsule can be retracted in the posterior using retractors or pins. After the labrum and osteophytes are removed, at least a partial view of the acetabulum should be available.

Providing an Acetabular Reamer

An acetabular reamer is provided to ream the natural acetabulum. The reamer is designed and adapted to be used with minimally invasive surgical techniques of the acetabulum. Specifically, the reamer is shaped to fit through the small incision at the surgical site. Further, the reamer is angled so the distal end properly engages the natural acetabulum with the correct angular orientation and without disrupting the incision and surrounding soft tissue.

Reaming the Acetabulum

Reaming of the acetabulum should begin with a reamer that is two sizes smaller than the preoperatively selected acetabular component size. A smaller reamer ensures that the fit does not exceed the anterior-posterior diameter. Of course, the reamer should not be so small that excessive anterior or posterior reaming occurs.

After an appropriately sized reamer is connected to the acetabular reamer, reaming should begin transversely toward the cotyloid notch. The ridges of the horseshoe (or medial osteophytes) should be removed. Reaming then continues in the position of desired anteversion while simultaneously creating a hemisphere. Larger reamers are used until the anterior and posterior rim of the acetabulum is contacted. The reamer should not be sunk below the superior rim of the bony acetabulum or reamed through the cortical bone of the cotyloid notch. Cancellous bone will be evident where the horseshoe ridges have been removed. The proper size trial shell should be selected according to the size of the reamer.

Providing an Acetabular Shell Impaction Instrument

An acetabular shell impaction instrument is provided to align and then impact the acetabular shell into the natural acetabulum. The instrument is designed and adapted to be used with minimally invasive surgical techniques of the acetabulum. Specifically, the instrument has a curved shape to fit through the small incision at the surgical site and precisely impact the implanted shell at the correct angular orientation. Further, this curvature enables the instrument to engage the shell in the acetabulum without disrupting the incision and surrounding soft tissue. Further yet, the instrument is adapted to move and align the acetabular shell while it is positioned in the acetabulum. It is important to position properly the shell before it is impacted and permanently seated in the acetabulum.

Inserting a Trial Shell Into the Acetabulum

The acetabular shell impaction instrument keys off the dome of the trial shell and is threaded or engaged in place. The instrument may offer anteversion and abduction references and rotational control. Preferably, the distal end of the instrument is adapted to mate with both the trial shell and implant shell in one single orientation. To connect the components, the distal end of the instrument is keyed and threadably attached to the trial shell. One skilled in the art will appreciate that the instrument, inserts, and shells can connect in various ways.

After the trial shell is inserted into the acetabulum, its position is verified through a trial window. The edge of the trial shell should be level with the anterior-inferior margins of the acetabulum and should completely fill the anterior-posterior bony acetabulum. The instrument can be used to move and align shell while it is positioned in the acetabulum. At this time, the trial shell can be manually tested to ensure that it is stable. If the trial is loose, then use the next larger size. If the trial is too tight, then ream the rim of the acetabulum. Importantly, the trial shell should be stable before selecting a similarly sized acetabular implant shell.

Inserting a Trial Insert Into the Trial Shell

Now, the trial insert is ready to be placed in the trial shell. An instrument is engaged in the rim of the trial insert and it is positioned inside the cavity of the trial shell. The trial insert contains a captured screw at the apex and can be threaded into the dome of the trial shell with a screwdriver or other tool. The trial components should be checked for proper fit and size.

At this point, the trials are removed from the surgical site. One skilled in the art, though, will appreciate that the trials could be temporarily left inserted to the natural acetabulum to articulate with a trial femoral prosthesis in a total hip replacement surgery.

Inserting an Implant Shell Into the Acetabulum

Some implant shells may be provided with flared rims and outer bone engaging spikes. In order to insert such a shell, cancellous bone slurry may be added within the acetabulum to fill existing bone cysts and provide an interface layer. Addition of this slurry typically occurs in total hip arthroplasty situations.

The acetabular implant shell is positioned into the acetabulum using the same acetabular shell impaction instrument used with the trial shell. Specifically, the distal connection end of the instrument is engaged and connected to the shell. The shell is partially inserted into the acetabulum until the rim begins to engage bone. The implant is then positioned with the instrument to the desired angular orientation, such as abduction and anteversion. Preferably, the shell is positioned with 20° to 25° of anteversion and with an abduction angle of about 35° to 45°. The anteversion can be verified using techniques known to those skilled in the art. The proximal impaction end of the instrument is then impacted with a mallet or similar instrument. Force from the mallet is transferred from the instrument to the shell as it is driven and permanently seated into the natural acetabulum. The shell should be driven into the acetabulum until the outer fixation spikes centrally engage into cancellous bone.

Figure 5:
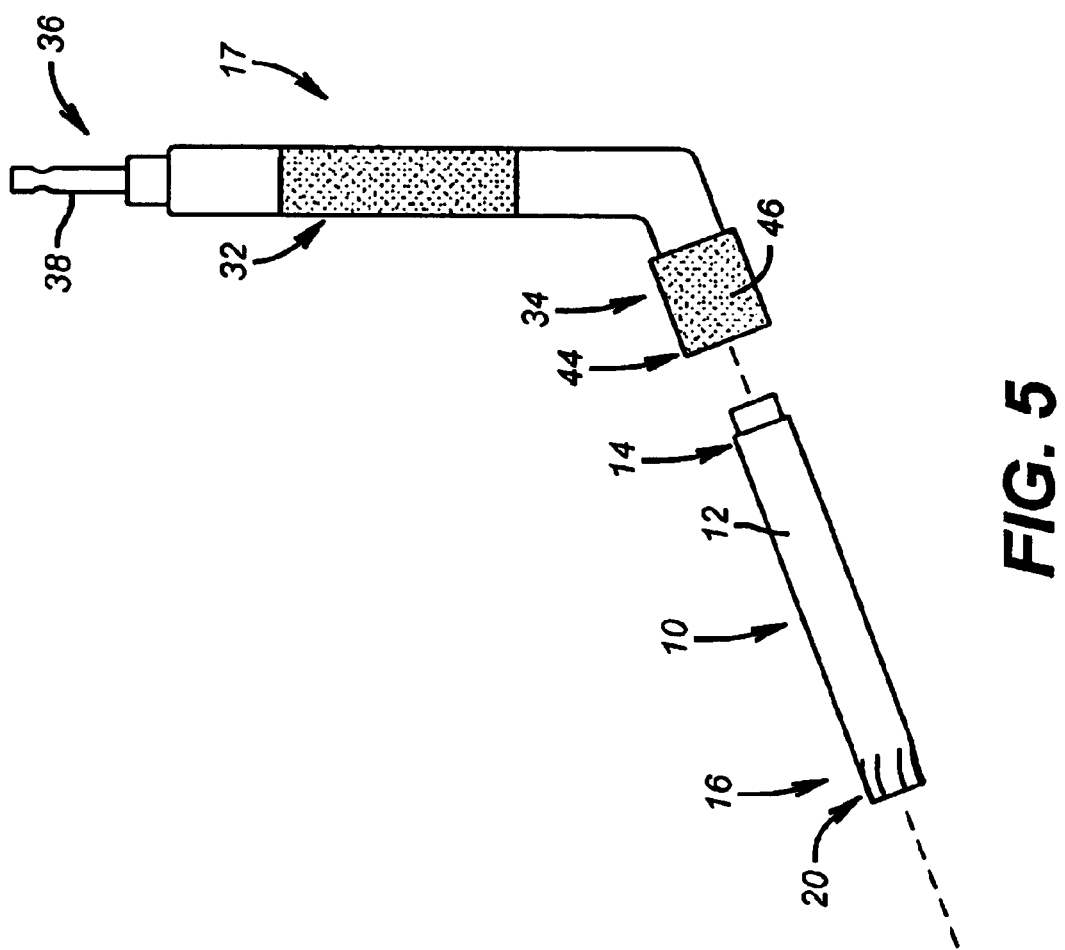
FIG. 5 is an exploded view of a driving bit of the present invention being connected to a fixed angled driving instrument.

Providing a Driving Instrument (See FIG. 5)

The driving instrument generally includes a working section and a driving section. The working section has a handle adapted to be gripped with a hand. A proximal end of the working section can be adapted to connect to a manual T-handle or adapted to connect to a device for automated driving. The driving section is formed at an angle with respect the working section and includes a distal end. This distal end has a standard AO interface connection and is adapted to removeably connect to the driving bit. The driving instrument preferably is a fixed angled driver or a flexible angled driver.

Figure 6:
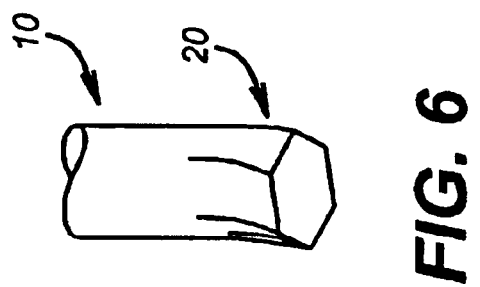
FIG. 6 is an enlarged view of the driving tip of the driving bit.

Providing A Driving Bit (See FIGS. 5–6)

The driving bit generally comprises an elongated, smooth cylindrical body that extends from a proximal end to a distal end. The proximal end has an interface or connection that is adapted to connect to the driving instrument. The distal end has a driving tip shaped as an interface or connection that is adapted to connect to an acetabular screw-plug, seal, dome plug, bone screw, or the like. Preferably, this end is shaped as a twisted hexagon.

Connecting the Driving Bit to the Driving Instrument (See FIG. 5)

The proximal end of the driving bit is connected to the distal end of the driving instrument. Both ends can be configured as an AO interface type connection. This connection is adapted to be removeable.

Figure 2B:
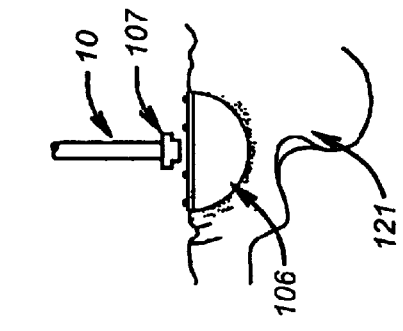
FIG. 2B is a view of an acetabular shell embedded in the acetabulum with a driving bit of the present invention inserting a dome plug or seal into the shell.
Figure 3:
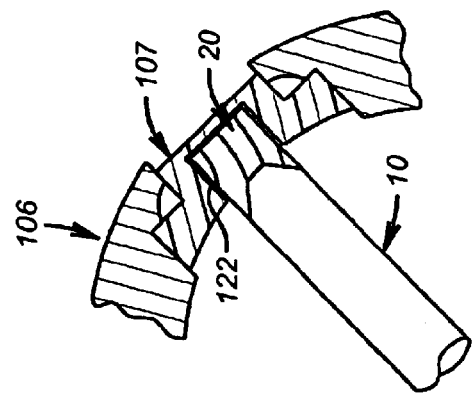
FIG. 3 is an enlarged view of an acetabular shell embedded in the acetabulum with a driving bit of the present invention inserting a screw plug or seal into the shell.

Removing Screw-Hole Plugs (See FIGS. 2B and 3)

The implant shell may be provided with screw-hole plugs, seals, or the like. In this instance, after the shell is properly seated in the acetabulum, one or more of the plugs may be removed with the driving bit. The driving instrument and attached driving bit are inserted through the incision, and the driving bit is engaged into the indentation of the plug. If the plugs are press-fit into the shell, then leverage is used to dislodge the screw-hole plug from the shell. If the plugs are screwed into the shell, then the driving bit is rotated to rotate the plug and remove it from the shell. The driving bit and attached screw-hole plug are removed from the surgical site.

Installing Screw-Hole Plugs and a Dome Hole Plug (See FIGS. 2B and 3)

The implant shell may be provided with screw-hole plugs or a dome plug that may be installed or inserted into the shell. Typically, these plugs have a head with a tool engaging recess. A threaded shaft extends from the head and is adapted to threadably engage a threaded bore in the acetabular shell.

The distal end of the driving bit is engaged with the plug. Specifically, the driving tip frictionally engages with the tool engaging recess in the plug. The plug and driving bit are then positioned into the surgical site so the threaded shaft on the plug engages the threaded bore in the acetabular shell. As the handle on the driving instrument is rotated, the driving bit simultaneously turns. The driving tip transfers torque to the plug and threads it into the threaded bore of the shell. Once the plug is fully threaded into the shell, the driving tip is disengaged from plug, and the driving bit is removed from the surgical site. At this time, another plug can be attached to the driving tip and the process is repeated as needed.

Figure 2A:
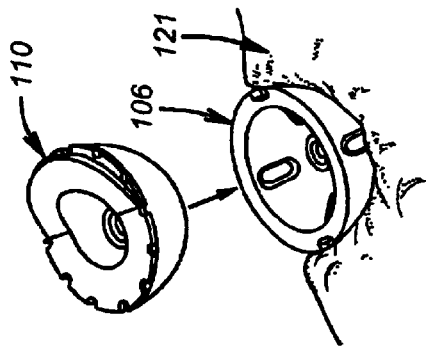
FIG. 2A is a sketch of an acetabular shell embedded in the acetabulum with a driving bit of the present invention inserting a bone screw through the shell.

Drilling Holes through the Acetabular Shell for Bone Screws (See FIG. 2A)

Next, a drill bit is provided, connected to a flexible driver, and positioned into the selected screw hole at an angle up to about 16°. As the hole or bore is drilled, care should be taken to protect the sciatic nerve and superior gluteal artery. A depth gauge may be inserted into the drilled holes to determine the depth for a corresponding bone screw. If desired, a tapping bit may be connected to the driver to tap the hole.

Installing Bone Screws through the Acetabular Shell (See FIG. 2A)

A bone screw is inserted through the acetabular shell in a manner similar to inserting a screw-hole plug or dome plug. The driving tip of the driving bit is engaged with the bone screw. Specifically, the driving tip frictionally engages with a tool engaging recess in the bone screw. This recess may be provided as a Phillip's type recess, hexagonal recess, or other recesses known in the art. The bone screw and driving bit are then positioned into the surgical site so the threaded shaft on the bone screw passes through the screw-hole opening in the acetabular shell and into a drilled hole. As the handle on the driving instrument is rotated, the driving tip simultaneously turns. The driving tip transfers torque to the bone screw and drives it through the screw-hole opening and into adjacent cortical bone of the natural acetabulum. The bone screw should be seated into the countersunk holes of the shell so the acetabular insert can properly snap into the shell. Once the bone screw is fully threaded into the shell, the driving tip is disengaged from bone screw, and the driving bit is removed from the surgical site. At this time, another bone screw can be attached to the driving tip and the process repeated as needed.

Figure 4:
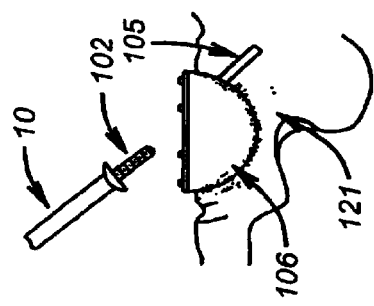
FIG. 4 is a view of an acetabular shell embedded in the acetabulum with an acetabular insert being connected to the shell.

Inserting and Impacting Insert into Shell (See FIG. 4)

Various inserts known to those skilled in the art (such as standard, hooded, and protrusion inserts) can be inserted into the implant shell. Once the appropriate size and style insert is selected, the insert is connected to an instrument. The insert is positioned into the cavity of the shell and should be rotated to align with the antirotational pegs on the shell. A surgical mallet is used to strike the proximal end of the instrument to seat the insert into the shell.

Closing Surgical Site

Once the insert is firmly connected to the shell, all instruments and devices are removed from the site. The acetabular shell and insert should now be properly positioned. Closure of the site may occur with well known techniques, such as posterior and anterior lateral approaches. Further, this disclosure will not discuss post-operative protocol or rehabilitation as such procedures are known in the art and tailored to meet the specific needs of the patient.

DETAILED DESCRIPTION OF DRIVING INSTRUMENT

One important advantage of the present invention is that the driving bit is specifically designed and adapted to be used in minimally invasive surgical techniques for aligning and driving acetabular plugs, seals, and bone screws into a prosthetic acetabular shell that is embedded into the natural acetabulum of a patient.

FIGS. 5 and 6 show the driving bit 10 of the present invention comprises an elongated body 12 having a straight cylindrical shape with a smooth outer surface. Body 12 extends from a proximal end 14 to a distal end 16. Proximal end 14 preferably has a standard connection or interface that is adapted to connect to an angled driving instrument 17. This connection is shown as an AO interface. Distal end 16 has a driving tip 20 that is adapted to connect to an acetabular shell component (see FIGS. 2A, 2B, and 3), such as a screw-hole plug, seal, dome plug, bone screw, or the like. Preferably, the driving tip 20 has a twisted hexagonal shape.

As best shown in FIGS. 3 and 6, the acetabular shell components generally have a head with a recess. The recess is shaped to receive the driving tip 20 of the driving bit 10. Preferably, this recess is a hexagonal recess. In order to connect the driving bit 10 to the shell component, the driving tip 20 is pressed into the recess formed in the head or proximal end of the shell component. The driving tip frictionally engages with this recess to firmly hold the shell component.

The proximal end 14 of the driving bit is connectable to the driving instrument 17. Preferably, this instrument is angled and includes a working section 32 and a driving section 34. The working and driving sections are disposed at an angle with respect to each other. A proximal end 36 of working section 32 has an interface 38 adapted to connect to a manual or automatic driving instrument. A distal end 44 of driving section 34 has a standard connection or interface 46. Preferably, this connection is an AO interface that is adapted to engage and removeably connect with the AO interface of proximal end 14 of driving bit 10.

Driving instrument 17 is shown as a fixed angle driver. One skilled in the art will appreciate that other driving instruments can also be utilized with the apparatus and method of the present invention. For example, the driving instrument can be provided as a flexible angled driver. Such drivers are known in the art.

One critical element of the present invention is the length of the driving bit 10. Preferably, this length is 1.25 inches and may have a range from about 0.37 inches to about 2.0 inches. Traditional driving bits are too short to work adequately in a MIS for implanting an acetabular shell. The driving bit must have a length that is long enough to extend into the very small surgical site and reach the inner wall of the acetabular shell embedded in the acetabulum. While installing a dome plug for instance, the driving bit must be long enough to reach the dome portion of the shell. If the driving bit is not long enough, then the dome plug may not be correctly attached or removed. Further, if the driving bit is not long enough, then bone screws may not be correctly driven to a proper depth into the acetabulum.

The driving tip is shown as a twisted hexagon, but it may be formed with various configurations known to those skilled in the art. This tip, for example, may be formed as a star, polygon, Phillip's screwdriver connection, or other configuration adapted to engage and hold a bone screw, screw-hole plug, dome plug, or the like.

It should be emphasized that although the method of the present invention was described with a specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention. Further, although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for using minimally invasive surgery to implant a prosthetic acetabular shell and insert into a natural acetabulum, comprising the steps of:

incising a hip with a minimally invasive incision;

implanting the acetabular shell into the natural acetabulum;

providing an angled driving instrument;

providing a driving bit having a length from about 0.37 inches to about 2.0 inches, wherein the driving bit has a distal end with a driving tip and a proximal end connected to the angled driving instrument;

attaching an acetabular plug to the driving tip of the driving bit;

positioning the driving bit and acetabular plug through the incision to engage the acetabular shell;

rotating the driving bit to threadably engage the acetabular plug to the acetabular shell;

removing the driving bit from the incision;

positioning the acetabular insert into the acetabular shell; and closing the incision.

2. The method of claim 1 wherein the step of incising a hip creates the minimally invasive incision with a length of about 2½ inches to about 4 to 5 inches.

3. The method of claim 2 further comprising the step of providing the driving bit with a length of about 1.25 inches.

4. The method of claim 3 further comprising the step of positioning the driving bit at an angle with respect to the driving instrument while the driving bit is positioned through the incision.

5. The method of claim 3 further comprising the step of providing the driving tip with a shape of a twisted hexagon.

6. The method of claim 5 further comprising the step of providing the driving bit with a cylindrical body having a smooth outer surface.

7. The method of claim 6 further comprising the step providing the proximal end of the driving bit with a removeable connection to the driving instrument.

8. The method of claim 7 further comprising the step of providing the proximal end with an AO interface.

9. A method for using minimally invasive surgery to implant a prosthetic acetabular shell into a natural acetabulum, comprising the steps of:

incising a hip with an incision having a length of between about 2½ inches to about 4 to 5 inches;

implanting the acetabular shell into the natural acetabulum;

providing an angled driving instrument;

providing a driving bit having a length from 0.37 inches to 2.0 inches, wherein the driving bit has a distal end with a driving tip and a proximal end removeably connectable to the angled driving instrument;

attaching an acetabular bone screw to the driving tip of the driving bit;

positioning the driving bit and acetabular bone screw through the incision to engage the acetabular shell;

driving the acetabular bone screw through the acetabular shell and into the natural acetabulum;

removing the driving bit from the incision; and closing the incision.

10. The method of claim 9 further comprising the step of providing the driving bit with a length of 1.25 inches.

11. The method of claim 9 wherein the step of providing the driving tip with a shape of a twisted hexagon.

12. The method of claim 11 further comprising the step of providing the driving bit with a cylindrical body having a smooth outer surface.

13. The method of claim 12 further comprising the step of providing the driving bit with an elongated straight body.

14. The method of claim 13 further comprising the step of providing the driving with an AO interface at the proximal end.

15. The method of claim 14 further comprising the steps of providing the driving instrument with a working section and positioning the driving bit at an angle with respect to the working section while the driving bit is connected to the driving instrument and while the driving bit is positioned through the incision.

16. A method for using minimally invasive surgery to connect an acetabular shell component to an acetabular shell that is embedded into a natural acetabulum, comprising the steps of:

incising a hip with an incision having a length of between about 2½ inches to about 4 to 5 inches;

providing an angled driving instrument;

providing a driving bit having a length from 0.37 inches to 2.0 inches, wherein the driving bit has a distal end with a driving tip and a proximal end removeably connectable to the angled driving instrument;

attaching the acetabular shell component to the driving tip of the driving bit;

positioning the driving bit and the acetabular shell component through the incision to engage the acetabular shell;

driving the acetabular shell component into the acetabular shell;

removing the driving bit from the incision; and closing the incision.

17. The method of claim 16 further comprising the step of providing the acetabular shell component as one of a screwhole plug, seal, dome plug, and bone screw.

18. The method of claim 17 further comprising the step of providing the driving bit with an elongated straight cylindrical shape.

19. The method of claim 18 further comprising the step of providing the driving tip with a hexagonal twisted shape.

20. The method of claim 19 further comprising the step of providing the driving bit with a length of about 1.25 inches.

* * * * *